United States Patent [19]

Fernandez de Castro et al.

[11] Patent Number: 4,481,094
[45] Date of Patent: Nov. 6, 1984

[54] STABILIZED POLYACRYLAMIDE GELS AND SYSTEM FOR SDS ELECTROPHORESIS

[75] Inventors: Aurora Fernandez de Castro, Union, Mich.; Jerry L. Neff, Nappanee, Ind.

[73] Assignee: TechAmerica Group, Inc., Elwood, Kans.

[21] Appl. No.: 548,042

[22] Filed: Nov. 2, 1983

Related U.S. Application Data

[63] Continuation of Ser. No. 378,902, May 17, 1982, abandoned.

[51] Int. Cl.$^3$ ............................................... C25B 7/00
[52] U.S. Cl. ............................ 204/180 G; 204/299 R
[58] Field of Search .......................... 204/180 G, 299 R

[56] References Cited

U.S. PATENT DOCUMENTS

| | | | |
|---|---|---|---|
| 3,384,564 | 5/1968 | Ornstein et al. | 204/180 G |
| 3,948,743 | 4/1976 | Monthoney et al. | 204/180 G |
| 4,246,084 | 1/1981 | Gurske | 204/180 G |
| 4,306,956 | 12/1981 | de Castro et al. | 204/180 G |

OTHER PUBLICATIONS

Weber et al., *J. of Biol. Chem.*, 244:4406, (1969), "The Reliability of Molecular Weight Determinations by SDS-Page".
Tamura et al., *J. Biochem.*, 71(3):543, (1972), "A New Buffer System for Disc Electrophoresis . . . Proteins".
Wyckoff et al., *Anal. Biochem.*, 78:459, (1977), "Polyacrylamide Gel Electrophoresis in SDS-. . . Procedure".
Catsimpoolas, Ed., *Methods of Protein Separation*, vol. 2, (1976).

*Primary Examiner*—Howard S. Williams
*Assistant Examiner*—T. L. Williams
*Attorney, Agent, or Firm*—John E. Benoit

[57] ABSTRACT

An improved polyacrylamide gel in a gel buffer, a system and method for conducting discontinuous sodium dodecyl sulfate electrophoresis is disclosed. The improved gel involves the use of a salt of 2-amino-2-methyl-1,3-propanediol at a pH of from 6.4 to 7.3 The improved process involves the use of the gel in combination with 2-amino-2-methyl-1,3-propanediol taurine as an electrolyte buffer at a pH of about 8.0 to 10.0.

5 Claims, No Drawings

STABILIZED POLYACRYLAMIDE GELS AND SYSTEM FOR SDS ELECTROPHORESIS

This application is a continuation of application Ser. No. 378,902, filed May 17, 1982, now abandoned.

BACKGROUND OF THE INVENTION

Electrophoresis in gels is a well-known procedure for determining the molecular weight of substances such as proteins, amino acids, nucleic acids, peptides and other macromolecules by applying an external electrical potential to a gel containing unresolved macromolecules in an electrophoresis cell and measuring the relative movements of the macromolecules. The molecular weight of a molecular specie can be calculated from a set of standards after obtaining a "Ferguson" plot to establish that the charge density of the unknown substance does not deviate from that exhibited by the standards.

The use of polyacrylamide gel electrophoresis (PAGE) allowed a separation effect based on a sieving effect imparted by control of the gel pore size in a "separating gel" layer, in addition to the separation obtained by differences in electrophoretic mobility. However, molecular weight determination by PAGE was complicated by the wide range of electrophoretic charges possessed by the macromolecules present in the system. It was then discovered that these charge differences could be negated by the addition of sodium dodecyl sulfate (SDS) to the system. Large numbers of SDS molecules associate with each protein or macromolecule; the charge of the SDS molecules imparted to the SDS-macromolecule complex is so large that differences in charge, due to the composition of the macromolecule, are not detectable.

A particularly useful electrophoresis procedure is discontinuous SDS-PAGE developed in 1964 (U.S. Pat. No. 3,384,564). Discontinuous SDS-PAGE involves the use of a multi-phasic (discontinuous buffer system, varying in chemical composition, i.e., change in pH and buffer discontinuities.

Often in discontinuous SDS-PAGE, two separately polymerized layers of polyacrylamide, designated as a "stacking gel" and a "separating gel", are prepared. The stacking gel contains a low polymer concentration and has a relatively large pore size. The large pore size allows the sample to concentrate into tightly packed zones. The separating gel contains higher polymer concentrations and has a relatively small pore size. The polymer is the result of reaction between monomer and co-monomer or cross-linking agent (percent C). The effective pore size of the polymer is an inverse function of "total monomer concentration", percent T, defined as the sum of the concentrations of acrylamide and cross-linking agent. The small pore size provides a restrictive effect and produces resolution of the sample.

The uniqueness of this kind of discontinuous SDS-PAGE consists of its ability to concentrate the sample into a narrow starting zone necessary for good resolution. This is achieved in the stacking gel which differs in ionic composition and pH from the buffers in the electrode vessels.

Concentration of the sample into a narrow starting zone produces good resolution and occurs as an interface develops when the leading ion from the buffer of the stacking gel migrates out while the trailing ion of the electrolyte buffer replaces it, both moving in the same direction. The leading ion is chosen to have a higher effective mobility than the ionic species of the sample, and therefore migrates in front of all other ions. Behind the leading ion other zones form and concentrate. The concentrated macromolecule in the samples appear to the eye as one thin "stack". The concentrated sample "stack" continues to migrate through the stacking gel with no change in characteristics until it encounters a discontinuity in entering the separating gel, either in the nature of the supporting medium, i.e., pore size, or in the buffer, e.g., pH. This change produces the separation of the difference macromolecular species into discrete bands. The overall procedure in discontinuous SDS-PAGE thus involves three stages: (a) stacking; (b) unstacking; and (c) resolution.

The $R_f$ is defined as the distance that each band component has traveled from the top of the separating gel to the center of the band, divided by the distance that the leading front has traveled. "Ferguson" plots of the log of $R_f$ versus the percent T of the separating gel are obtained to check for systematic errors. The molecular weight of a particular macromolecule can be calculated by plotting a function of $R_f$ versus a function of molecular weight for a series of known standards. After measuring the $R_f$ for the unknown, one can read the molecular weight from such standard curve.

To carry out a discontinuous SDS-PAGE, the gels are placed in a chamber containing buffer solutions, and the sample is placed on top of the stacking gel and under the upper electrolyte buffer. After an electrical potential is applied, the sample is electrophoresed. The separated macromolecular bands are then stained for visualization. A tracking dye can be added to help monitor the electrophoresis time and to help in the measurement of the relative distance ($R_f$) of the bands.

Resolution in SDS-PAGE depends on the separation between any two bands of interest and their respective bands widths. The relative mobilities of the constituents at a given pH are very important as they delineate the borders of the moving boundary which is either to stack or to unstack the protein of interest. At a particular pH the particular ionic species in the buffer system determines their electrophoretic mobilities and the electrophoretic resolution of the different proteins.

Polyacrylamide gels are prepared by polymerizing polyacrylamide monomers with a cross-linking agent in the presence of a gel buffer. Polyacrylamide gels are relatively unstable, causing the gels to deteriorate after relatively short periods of time. There is a need for a stabilized polyacrylamide gel which can be prepared and stored for extended periods of time. There is need for a buffer system that in conjunction with such gels and in the presence of SDS will separate proteins by their molecular size.

DESCRIPTION OF THE PRIOR ART

*J. Biol. Chem.*, 244(16):4406–4412 (1969) describes the preparation of polyacrylamide gels in a sodium phosphate gel buffer. The gels apparently were prepared shortly before use. A dilute sodium phosphate solution was used as the electrolyte buffer.

A brochure published by LKB Instrument Co. (April 1977) entitled "SDS and Concentrated Polyacrylamide Gel Electrophoresis with LKB 2117 Multiphor" describes the use of a sodium phosphate gel buffer at a neutral pH. The publication recommends that the gel prepared be used within four days. Apparently diluted sodium phosphate was used as the electrolyte.

A common SDS-PAGE system uses tris-(hydroxymethyl)aminomethane chloride at a pH of 8.9 in combination with tris-(hydroxymethyl)aminomethane glycine as an electrolyte at a pH of 8.6.

J. Biochem. 71:543-545 (1972) describes the use of a polyacrylamide gel with a buffer of 2-amino-2-methyl-1,3-propanediol chloride, designated "ammediol" chloride, at a pH of about 9.5, in conjunction with ammediol glycine as the electrolyte, at a pH of 8.8, in a non-SDS system. Analytical Biochem., 76:459-482 (1977) describes a similar ammediol chloride-ammediol glycine system for a SDS-PAGE procedure. No pH range before electrophoresis was described.

National Technical Information Service, Springfield, Va. 22151, has available PB No. 196090 entitled "Multiphasic Buffer Systems Output" which is a computerized print-out listing over four thousand buffer systems. Among the compositions disclosed is a system of buffers containing ammediol, chloride ions, taurine and bicine ions. The pH range is indicated as being 7.5 to 10.6; a preferred pH is 9.2.

None of the articles described above disclose or suggest that polyacrylamide gels can be stabilized in the presence of a gel buffer of a salt of 2-amino-2-methyl-1,3l-propanediol at a pH of between 6.4 to 7.3, or the combination of this gel buffer and 2-amino-2-methyl-1,3-propanediol taurine at a pH of about 8.0 to 10.0 as an electrolyte buffer. None of the references suggest the use of such a system with SDS for the successful separation of proteins.

SUMMARY OF THE INVENTION

The present invention is directed to an improved stabilized polyacrylamide gel in a gel buffer, a system and a method for conduction discontinuous SDS-PAGE. The gel buffer is a salt of 2-amino-2-methyl-1,3-propanediol at a pH of 6.4 to 7.3. The system and method include the stabilized gel and 2-amino-2-methyl-1,3-propanediol taurine as an electrolyte buffer at a pH of about 8.0 to 10.0, in the presence of SDS to separate proteins by their sizes or molecular weights.

DETAILED DESCRIPTION OF THE INVENTION

As indicated earlier, a discontinuous SDS-PAGE system often requires preparation of two separately polymerized layers of acrylamide gel, the separating gel and the stacking gel.

The separating gel was prepared by the following method. Commercially available acrylamide, the solvent-recrystallized form, or recrystallized from acetone (See Methods of Protein Separation, Vol 2, (1976)) was mixed with a cross-linking agent such as N,N'-methylenebisacrylamide ("Bis") or N,N'-diallyltartardiamide; a free-radical catalyst activator such as potassium persulfate, riboflavin and N,N,N',N'-tetramethylethylenediamine and the gel buffer used in the present invention, a salt of 2-amino-2-methyl-1,3-propanediol.

Adjustment of the pH of the gel buffer to the range 6.4 to 7.3 has been found to be a critical limitation. The 2-amino-2-methyl-1,3-propandiol salt is prepared by the addition of a strong acid, e.g., hydrochloric, sulfuric, nitric, or hydrofluoric acid to the propanediol compound. Propanediol salts of chloride and sulfate are preferred. This forms a salt solution which can be adjusted to a pH of about 6.4 to 7.3. If the pH of the buffer is much above 7.3, or below 6.4, the acrylamide gel is unstable soon after being prepared and deteriorates so as to be unusable in electrophoresis and the protein bands are not clearly resolved. In a preferred embodiment of the invention, the polyacrylamide gel is prepared in a gel buffer of pH 6.7 to 7.1.

A useful range of acrylamide monomer concentration is from about ½ to 30 percent T. A more commonly used range is from 4 to 15 percent.

The separating gel solutions were dispensed in a rectangular mold (slab) or in a tube, a layer of water or buffer was placed on the surface to avoid a meniscus forming on the gel surface and the gels were allowed to solidify. After the separating gels solidified and the liquid layer was removed, an acrylamide stacking gel mixture, made with the same buffer at about neutral pH was prepared and dispensed on top of the separating gel in the gel tube or slab and allowed to polymerize. A layer of water or buffer was placed over the stacking gel to provide a flat surface. The final monomer concentration of the stacking gel is not critical as long as it is lower than the separating gel. This stacking gel was sometimes omitted.

A macromolecular sample was mixed with SDS, buffer and optionally a density-increasing agent e.g., glycerol, sucrose or urea. A reducing agent, e.g., dithiothreitol (DTT) o mercaptoethanol can be added. An amount of tracking dye, e.g., thymol blue, etc., that is visually detectable can be added to the sample to easily follow the course of the electrophoresis. The mixture was heated to a range of about 90° to 100° C. for about 5 minutes. The heating step causes denaturation of the molecules and enables the SDS, which is an ionic detergent, to complex with the macromolecules, providing them with a large negative net charge density.

The liquid layer on top of the gel was removed, and a sample mixture placed on top of the stacking gel or separating gel if no stacking gel was present. The electrolyte buffer, 2-amino-2-methyl-1,3-propanediol taurine at a pH of between 8 to 10, was then placed so that both ends of the gel were in contact with the electrolyte buffer. The samples were then subjected to electophoresis at a constant current of about 2 to 5 milliamps per sample and the electrophoresis allowed to proceed until the tracking dye had reached approximately the bottom of the gel or for a specified period of time. The gels were removed from the electrophoresis apparatus, placed in a fixing solution and stained to visualize the bands of separated macromolecules. The gels were then destained to remove the background. The $R_f$ was measured and the molecular weight determined.

The gels that are to be stored for use at another time are stored in a storage buffer of similar composition to the gel buffer to prevent drying out of the gels, and usually containing some preservative to prevent bacterial growth.

EXAMPLE I

A. Preparation of Separating Gel

A 0.3M solution of the ammediol chloride buffer at a pH of 6.7 to 6.9 was prepared by mixing together ammediol with hydrochloric acid. This solution also contained approximately 300 µl N,N,N', N'-tetramethylethylenediamine per 100 ml of solution. This solution was mixed with an aqueous solution of acrylamide and N,N'-methylenebisacrylamide (Bis), ammonium persulfate and water. The acrylamide-Bis mixture was prepared by adding 38.9 g acrylamide and 1.1 g Bis to 100 ml H$_2$O. The catalyst solution was prepared by adding 140 mg of ammonium persulfate in 100 ml H$_2$O. When the above components were mixed in equal quantities, a gel having about 10 percent T was produced. A 150 mm gel tube was filled to about 100 mm height with the mixture and allowed to solidify.

B. Preparation of Stacking Gel

The stacking gel was prepared by mixing together the above buffer solution, $H_2O$, the above ammonium persulfate catalyst, riboflavin catalyst, and acrylamide-Bis mixture in a proportion of 2:2:1:1:2 respectively. The riboflavin catalyst was prepared by adding 2 mg of riboflavin to 100 mg $H_2O$. The acrylamide-Bis mixture was prepared by adding 10 g acrylamide and 2.5 g Bis to 100 ml water.

C. Preparation of Electrolyte Buffer

The electrolyte buffer was prepared by mixing ammediol with taurine to produce a buffer of about 0.02M ammediol and 0.04M taurine at a pH of approximately 8.7.

D. Preparation of Reaction Mixture

A mixture of several proteins was prepared by mixing myosin (M.W. 194,000), β-galactosidase (M.W. 116,000), phosphorylase B (M.W. 94,000), bovine serum albumin, (BSA, M.W. 67,000), aldolase (M.W. 43,000), carbonic anhydrase (M.W. 30,000), soybean trypsin inhibitor (M.W. 21,500), lysozyme (M.W. 14,700) in an approximate concentration of 400 μg of protein/ml in 40–50 percent glycerol. The sample mixture was then prepared using the above marker protein mix, sodium dodecyl sulfate (SDS) solution (4 gm to 100 ml $H_2O$), 0.36 mM dithiothreitol solution, glycerol, sample buffer of ammediol chloride (0.06M, pH 7.0) and water in a 1:1:1:1:1:3 ratio. The mixture also contained a small amount of thymol blue as a tracking dye. The mixture was incubated at 95°–100° C. for about five minutes. Forty microliters of the incubated mixture were then layered on the gels and eletrophoresed. The eletrophoresis was run at about 2 milliamps per gel for about 3½ to 3¾ hours. The gels were then fixed in 12 percent trichloroacetic acid, stained with Coomassie Blue, destained and the molecular weight of the proteins plotted as described below.

The Coomassie Blue stain contained 32 percent methanol, 28 percent glacial acetic acid and 4 percent Coomassie Blue R250. The solution was mixed for three hours until the dye dissolved. One part of this staining solution to 3 parts $H_2O$ was used to stain the bands.

The destaining solution was prepared by mixing 140 ml glacial acetic acid and 100 ml methanol and adding water to a total of 2liters.

The gels were removed from the trichloroacetic acid, rinsed in water and placed in the diluted (1:3) staining solution for about 2 hours at approximately 60° C. The gels were removed from the staining solution, rinsed with water and placed in the destaining solution.

Calculation of the $R_f$ values and their plot versus the log of molecular weight of the macromolecules indicated that the system successfully separated the proteins. In addition good values of molecular weight resulted when the standard curve was made from seven of the eight proteins in the mixture and the eight used as the unknown.

For long storage the gels are kept in a storage buffer containing 3.15 gm ammediol chloride pH 6.8 ±0.2 and 20 mg merthiolate in 400 ml $H_2O$.

EXAMPLE II

A. Preparation of Separating Gel

A mixture of a buffer solution of about 0.2 M ammediol sulfate at a pH of from 6.4 to 7.3, was prepared as described in Example I, except sulfuric acid was used in placed of hydrochloric acid. This solution also contained approximately 300 μl N,N,N',N'-tetramethylethylenediamine per 100 ml solution. The above solution was mixed with an aqueous solution of acrylamide and Bis (40 percent T, 2.75 percent C), ammonium persulfate solution (0.2 percent) and water. The above components were mixed in a 2:1:2.5:2.5 proportion to obtain a 5 percent T gel. A 150 mm gel tube was filled to about 100 mm height with the mixture and allowed to solidify for about 45 minutes.

B. Preparation of Stacking Gel

The stacking gel was prepared by mixing the above buffer solution, $H_2O$, ammonium persulfate (0.2 percent), and acrylamide-Bis solution (12.5 percent T, 20 percent C) in equal proportions.

C. Preparation of Electrolyte Buffer

The ammediol taurine electrolyte buffer of varied concentration was prepared similar to Example I; the pH was between about 8.0 to 10. The electrolyte buffer also contained SDS in the amount of about 12 ml of a 4 percent SDS solution per liter of electrolyte buffer.

D. Preparation of Reaction Mixture

A similar mixture of proteins as in Example I was made except that aldolase having a molecular weight of 40,000 was substituted for ovalbumin of molecular weight 43,000. This sample mixture was mixed with 4 percent SDS solution, 0.36 mM DTT solution, glycerol, sample buffer of ammediol chloride (0.06M, pH 7.0) and water in a 1:1:1:1:1:3 ratio. The mixture also contained a small amount of thymol blue as the tracking dye. The mixture was incubated at 95°–100° C. for about five minutes. Twenty microliters of the incubated mixture were then layered on the gels and electrophoresed. The electrophoresis was run at about 2.5 milliamps per gel. When electrophoresis was finished, the gels were fixed, stained and destained successively as described in Example I. The $R_f$ of the bands were measured. The clear separation of the protein bands indicated a successful run.

The acrylamide gels were stored in an ammediol buffer with the same final concentration as the gel buffer at a pH of from 6.4 to 7.3 for up to one year at 5° C., and for six months at room temperature. The gels were stable under these storage conditions; electrophoresis of macromolecules using the gels stored under these conditions produced sharp bands and good reproducibility of the molecular weight determinations.

For comparative purposes, acrylamide gels were prepared and macromolecular samples similar to those described in Examples I and II were subjected to electrophoresis using the systems described below. The pH of the separating gel was in the range of 6.4 to 7.3 to avoid hydrolysis of the polyacrylamide gel.

TABLE I

| Gel Buffer | Electrolyte |
|---|---|
| (1) Tris(hydroxymethyl)- amino methane chloride | Tris(hydroxymethyl)amino- methane glycine |
| (2) 2-amino-2-methyl-1,3- propanediol chloride | 2-amino-2-methyl-1,3- propanediol boric acid |
| (3) 2-amino-2-methyl-1,3- propanediol chloride | 2-amino-2-methyl-1,3- propanediol asparagine |

In the above systems, the electrophoresis results were unsatisfactory. The individual protein bands of the mixture of protein markers used were unsatisfactorily diffuse. In addition, there were problems of non-linearity of the differences traveled by the protein markers, and large voltage changes during the electrophoresis.

What is claimed is:

1. A buffer system for conducting discontinuous sodium dodecyl sulfate polyacrylamide gel electrophoresis, comprising (a) a stabilized polyacrylamide gel medium containing a gel buffer of a salt of 2-amino-2-methyl-1,3-propanediol at a pH of about 6.4 to 7.3, and (b) 2-amino-2-methyl-1,3-propanediol taurine, at a pH of about 8.0 to 10.0 as an elctrolyte buffer.

2. A buffer system as claimed in claim 1 wherein the 2-amino-2-methyl-1,3-propanediol has a pH of about 6.8 to 7.1.

3. A buffer system as claimed in claim 1 wherein the gel buffer is selected from the group consisting of 2-amino-2-methyl-1,3-propanediol chloride, sulfate, nitrite and fluoride.

4. A buffer system as claimed in claim 3 wherein the gel buffer is 2-amino-2-methyl-1,3-propanediol chloride or sulfate.

5. In a discontinuous sodium dodecyl sulfate polyacrylamide gel electrophoresis process for determining the molecular weight of a macromolecule which includes the steps of mixing the macromolecules with sodium dodecyl sulfate, adding the mixture to a polyacrylamide gel medium containing acrylamide monomers in a gel buffer, placing the gel medium in contact with an ioncontaining electrolyte solution, subjecting the macromolecules and gel medium to a differential electrical potential to produce migration of the macromolecules and electrolyte ions and determining the molecular weight of said macromolecule, the improvement which comprises using as the gel buffer a salt of 2-amino-2-methyl-1,3-propanediol at a pH of about 6.4 to 7.3 and using as an electrolyte buffer 2-amino-2-methyl-1,3-propanediol taurine at a pH of about 8.0 to 10.0.

* * * * *